United States Patent
Schmitt

(10) Patent No.: US 8,850,676 B2
(45) Date of Patent: Oct. 7, 2014

(54) GUIDEWIRE LOADING TOOL FOR A CATHETER

(75) Inventor: Joshua Schmitt, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 831 days.

(21) Appl. No.: 13/032,796

(22) Filed: Feb. 23, 2011

(65) Prior Publication Data

US 2012/0210569 A1  Aug. 23, 2012

(51) Int. Cl.
| | |
|---|---|
| *B23B 3/16* | (2006.01) |
| *B23B 7/04* | (2006.01) |
| *A61B 18/04* | (2006.01) |
| *A61B 17/02* | (2006.01) |
| *A61M 25/09* | (2006.01) |
| *B23P 19/00* | (2006.01) |

(52) U.S. Cl.
CPC ............................... *A61M 25/09041* (2013.01)
USPC .................... 29/44; 606/167; 606/33

(58) Field of Classification Search
USPC ...................... 29/244; 606/167, 33
See application file for complete search history.

(56) References Cited

U.S. PATENT DOCUMENTS

| | | | |
|---|---|---|---|
| 5,425,710 A * | 6/1995 | Khair et al. | 604/103.05 |
| 5,871,444 A * | 2/1999 | Ouchi | 600/374 |
| 6,110,146 A | 8/2000 | Berthiaume | |
| 6,793,648 B2 * | 9/2004 | Oslund et al. | 604/160 |
| 2003/0036768 A1 * | 2/2003 | Hutchins et al. | 606/170 |
| 2003/0212373 A1 * | 11/2003 | Hall et al. | 604/263 |
| 2004/0073193 A1 | 4/2004 | Houser et al. | |
| 2005/0090847 A1 * | 4/2005 | Hutchins et al. | 606/167 |
| 2006/0094987 A1 | 5/2006 | van Erp et al. | |
| 2007/0162102 A1 * | 7/2007 | Ryan et al. | 623/1.12 |
| 2008/0082051 A1 | 4/2008 | Miller et al. | |
| 2010/0094087 A1 * | 4/2010 | Hutchins et al. | 600/117 |
| 2012/0296327 A1 * | 11/2012 | Hutchins et al. | 606/33 |

\* cited by examiner

*Primary Examiner* — Lee D Wilson
*Assistant Examiner* — Alvin Grant

(57) ABSTRACT

A removable guidewire funnel tool aids in backloading a catheter onto a guidewire. The guidewire funnel tool includes a pliable loading coupler having a lumen therethrough. The lumen has a tapered distal section that serves to receive a guidewire and a tapered proximal section that receives and couples with a correspondingly tapered distal tip of the catheter. The guidewire funnel tool has a longitudinal slot or area of weakness along the entire length of the loading coupler and a grip tab to enable easy removal of the guidewire funnel tool after the guidewire lumen of the catheter is loading with the guidewire.

17 Claims, 6 Drawing Sheets

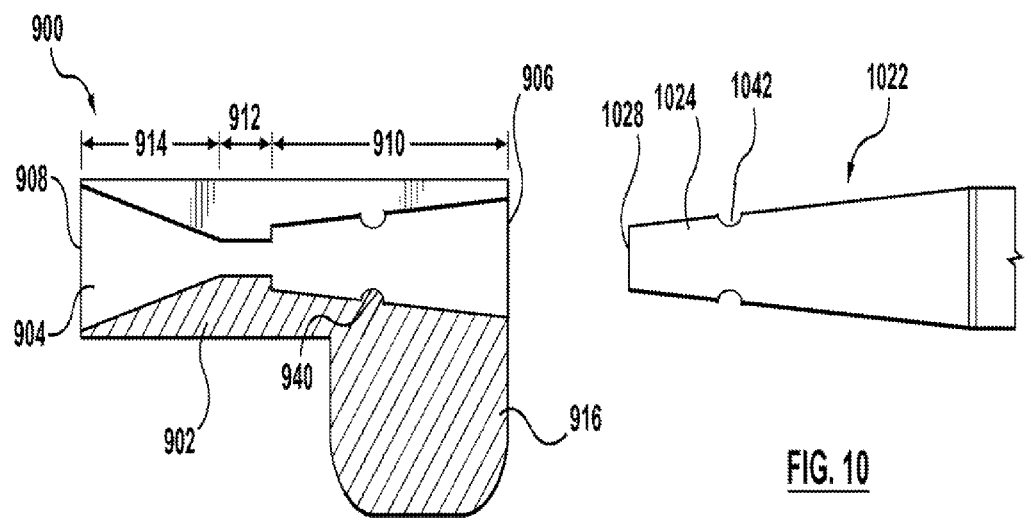

GUIDEWIRE LOADING TOOL FOR A CATHETER

The invention relates in general to a catheter having a guidewire lumen, and in particular to a guidewire loading tool that aids in cannulating a guidewire lumen of a catheter.

BACKGROUND

Medical guidewires are used in numerous catheterization procedures as an aid to placement of a catheter and/or prosthesis at a selected site within a body lumen. Among the more common uses of guidewire is in the catheterization of blood vessels for diagnostic or therapeutic purposes.

Guidewires may be extremely slender, in the order of 0.25 to 0.89 mm (0.010 to 0.035 inches) in diameter. The guidewire lumen in the catheter has a diameter slightly greater than the guidewire. Cannulating the guidewire lumen of the catheter with a guidewire is often difficult due to the small dimension of the guidewire, the small dimension of the guidewire entry port, and the relatively delicate nature of these components. Inserting the guidewire into the guidewire lumen may be as difficult as threading a needle. Accordingly, there is a need in the art for a tool to assist in the insertion of a guidewire into a catheter.

SUMMARY

Embodiments hereof relate to a guidewire funnel tool to aid in backloading a guidewire into a guidewire lumen of a catheter. The guidewire funnel tool includes a pliable cylindrical loading coupler having a guidewire insertion end, a catheter insertion end, and a continuous lumen extending therebetween. The lumen has tapered regions on opposing sections thereof with a tapered distal section that serves to receive the guidewire and a tapered proximal section to receive and couple with a distal tip of the catheter and to further align the distal tip of the catheter with a constant diameter middle section of the lumen. The guidewire funnel tool lumen is configured such that the straight middle section of the lumen straightens and stabilizes the guidewire received from the tapered distal section of the lumen prior to the guidewire entering the distal tip of the catheter being held by the tapered proximal section of the lumen. The cylindrical loading coupler includes an area of weakness formed along a length thereof, and a tab that radially extends therefrom. The tab is adapted to be gripped by a user in order to remove the pliable loading coupler from the loaded catheter via the area of weakness.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 9 is a sectional side view of a guidewire funnel tool according to another embodiment hereof, wherein the guidewire funnel tool includes a circumferential groove formed on an inner surface thereof.

FIG. 10 is a side view of a tip of a catheter having a circumferential protrusion thereon for use with the guidewire funnel tool of FIG. 9.

DETAILED DESCRIPTION

Specific embodiments are now described with reference to the figures, wherein like reference numbers indicate identical or functionally similar elements. The terms "distal" and "proximal" are used in the following description with respect to a position or direction relative to the catheter on which the guidewire funnel tool is to be used. "Distal" or "distally" are a position distant from or in a direction away from the catheter. "Proximal" and "proximally" are a position near or in a direction toward the catheter.

The following detailed description is merely exemplary in nature and is not intended to limit the invention or the application and uses of the invention. Although the description of the embodiments is in the context of loading a guidewire into a catheter, the embodiments may also be used in any other applications where it is deemed useful. Furthermore, there is no intention to be bound by any expressed or implied theory presented in the preceding technical field, background, brief summary or the following detailed description.

Figure 1:
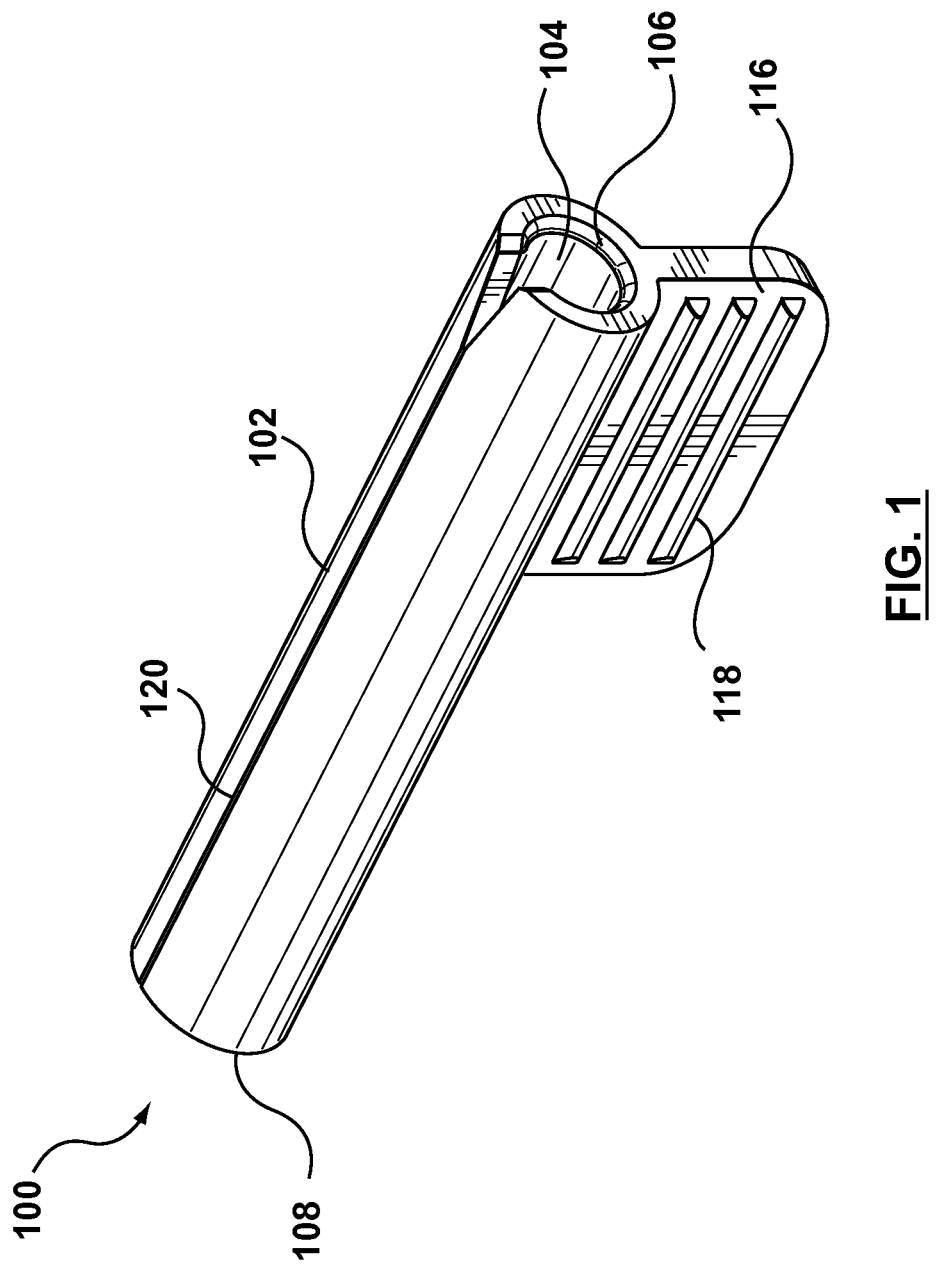
FIG. 1 is a perspective view of a guidewire funnel tool according to an embodiment hereof.
Figures 2, 2A:
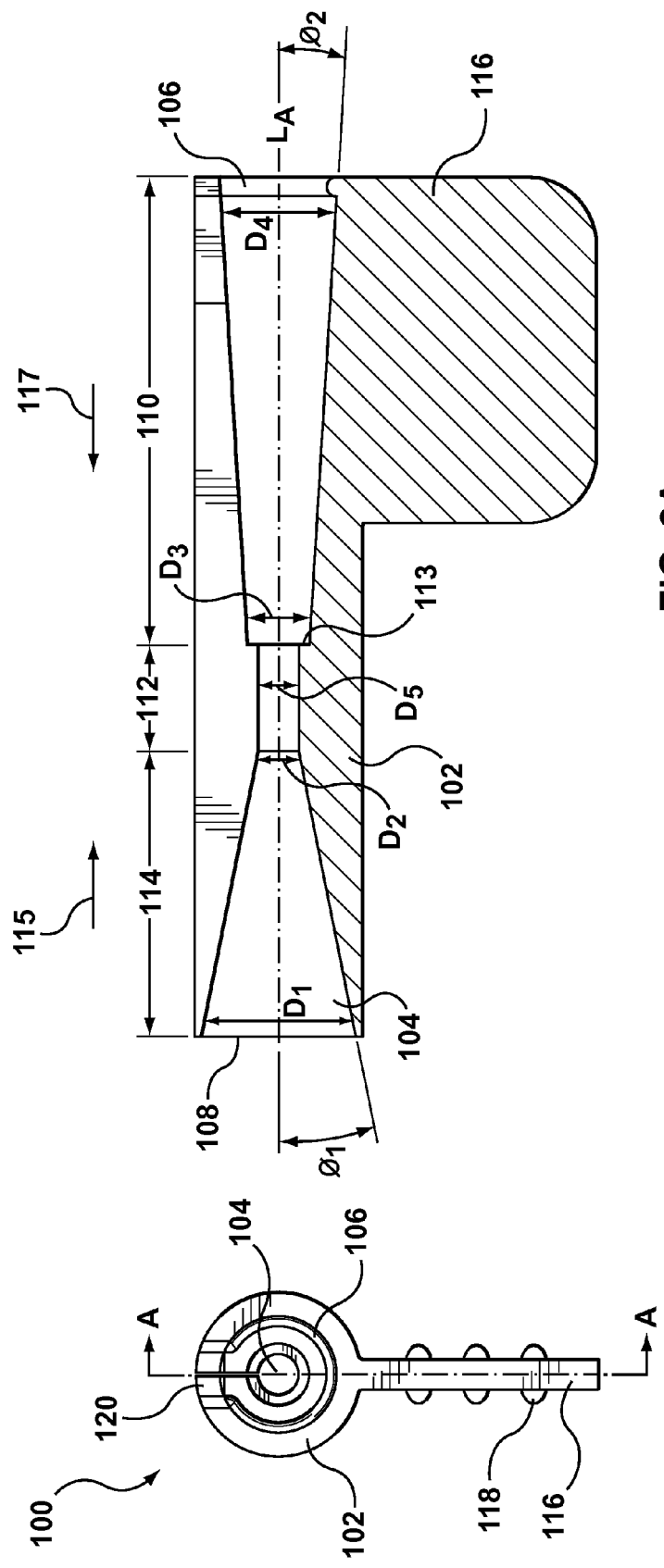
FIG. 2 is an end view of the guidewire funnel tool of FIG. 1.
FIG. 2A is a sectional side view of the guidewire funnel tool of FIG. 1, the sectional view taken along line A-A of FIG. 2.

Embodiments hereof relate to a removable guidewire funnel tool that aids in backloading a catheter or other intravascular delivery system onto a guidewire. With reference to FIG. 1, as well as the end view of FIG. 2 and the sectional view of FIG. 2A taken along line A-A of FIG. 2, a guidewire funnel tool 100 includes a loading coupler 102 and a grip tab 116. Grip tab 116 is a generally rectangular piece of material that radially extends from an outside surface of loading coupler 102. When in use, guidewire funnel tool 100 may be covered in fluids such as saline, blood, and/or hydrophilic coating and is often slippery, which could make it difficult to remove. Grip tab 116 provides means for the user to effectively grasp and remove guidewire funnel tool 100 when desired. Grip tab 116 may include a plurality of tactile gripping elements 118 on opposing faces or surfaces thereof for enhancing a user's ability to grasp and pull grip tab 116. Gripping elements 118 may be for example longitudinal ribs, protrusions of other shapes or geometries, or grooves formed within surfaces of grip tab 116. In an embodiment, loading coupler 102, grip tab 116, and gripping elements 118 are integrally formed from a single piece of flexible and pliable material such as polyurethane, PEBAX, polyethylene, polypropylene, fluorocarbon polymers or like biocompatible polymeric materials. For example, loading coupler 102, grip tab 116, and gripping elements 118 may be formed as a single molded component. In another embodiment, loading coupler 102, grip tab 116, and/or gripping elements 118 may be two or more separate components of the same or different materials that are coupled together via any suitable mechanical method such as via an adhesive. As will be explained in more detail herein, at least loading coupler 102 is constructed from a pliable and flexible material such that guidewire funnel tool 100 retains its shape while being cannulated with a guidewire while simultaneously being deformable when guidewire funnel tool 100 is to be removed from the catheter after a guidewire has been successfully inserted into a guidewire lumen thereof. In one embodiment, the pliable and flexible material is an elastomeric material.

Loading coupler 102 is a tubular body or component having a longitudinal axis $L_A$ that defines a continuous lumen 104 extending the entire length thereof between a guidewire insertion end or port 108 to a catheter insertion end or port 106. Grip tab 116 is positioned along loading coupler 102 proximate catheter insertion end 106. In an embodiment, loading coupler 102 has an outer diameter of approximately 0.175 inches. An inner diameter of loading coupler 102, i.e., the diameter of lumen 104, varies along the length of loading coupler 102. More particularly, as shown in the sectional view of FIG. 2A, lumen 104 includes a tapering first or distal section 114, a straight second or middle section 112, and a tapering third or proximal section 110. It will be understood by one of ordinary skill in the art that sections 110, 112, and 114 form continuous lumen 104 through loading coupler 102 but are described with separate reference numbers for clarity.

Distal section 114 of lumen 104 tapers in a proximal direction toward a midpoint of loading coupler 102 as indicated by reference arrow 115 from a first, relatively larger, diameter $D_1$ to a second, relatively smaller, diameter $D_2$. Diameter $D_1$ is preferably between 50% and 200% greater than an outer diameter of a guidewire that is to be slidingly received within guidewire funnel tool 100 while diameter $D_2$ is preferably only slightly larger than an outer diameter of a guidewire that is to be slidingly received within guidewire funnel tool 100. For example, in one embodiment diameter $D_2$ may be approximately 0.045 inches. The inner surface of distal section 114 tapers at an angle $\emptyset_1$ with respect to longitudinal axis $L_A$. In one embodiment, angle $\emptyset_1$ may be approximately 10°.

Middle section 112 of lumen 104 has a cylindrical shape with a substantially constant diameter $D_5$ that is only slightly larger than an outer diameter of a guidewire that is to be slidingly received within guidewire funnel tool 100. For example, in one embodiment diameter $D_5$ may be approximately 0.045 inches.

Proximal section 110 of lumen 104 tapers in a distal direction toward the midpoint of loading coupler 102 as indicated by reference arrow 117 from a first, relatively larger, diameter $D_4$ to a second, relatively smaller, diameter $D_3$. The inner surface of proximal section 110 tapers at an angle $\emptyset_2$ with respect to longitudinal axis $L_A$. In one embodiment, angle $\emptyset_2$ may be approximately between 3° and 5°. As will be explained in more detail herein, angle $\emptyset_2$, diameter $D_3$, and diameter $D_4$ are selected to imitate the profile of a tapered distal tip of a catheter. In the embodiment shown in FIG. 2A, diameter $D_3$ of proximal section 110 is slightly larger than diameter $D_5$ of middle section 112 such that a stepped surface 113 is formed along lumen 104 against which a distalmost surface of the catheter distal tip abuts.

The length of distal section 114 may range between 30% and 40% of the total length of loading coupler 102, the length of middle section 112 may range between 5% and 15% of the total length of loading coupler 102, and the length of proximal section 110 may range between 50% and 65% of the total length of loading coupler 102. In an embodiment, distal section 114 is approximately ⅓ of the total length of loading coupler 102, middle section 112 is approximately ⅑ of the total length of loading coupler 102, and proximal section 110 is approximately ⅝ of the total length of loading coupler 102. However, it will be understood by one of ordinary skill in the art that the relative lengths of distal section 114, middle section 112, and proximal section 110 may vary according to intended application. In an embodiment, loading coupler 102 has a length of approximately 0.90 inches with lumen 104 having distal section 114 of a length of approximately 0.30 inches, middle section 112 of a length of approximately 0.10 inches, and proximal section 110 of a length of approximately 0.50 inches.

Figure 3:
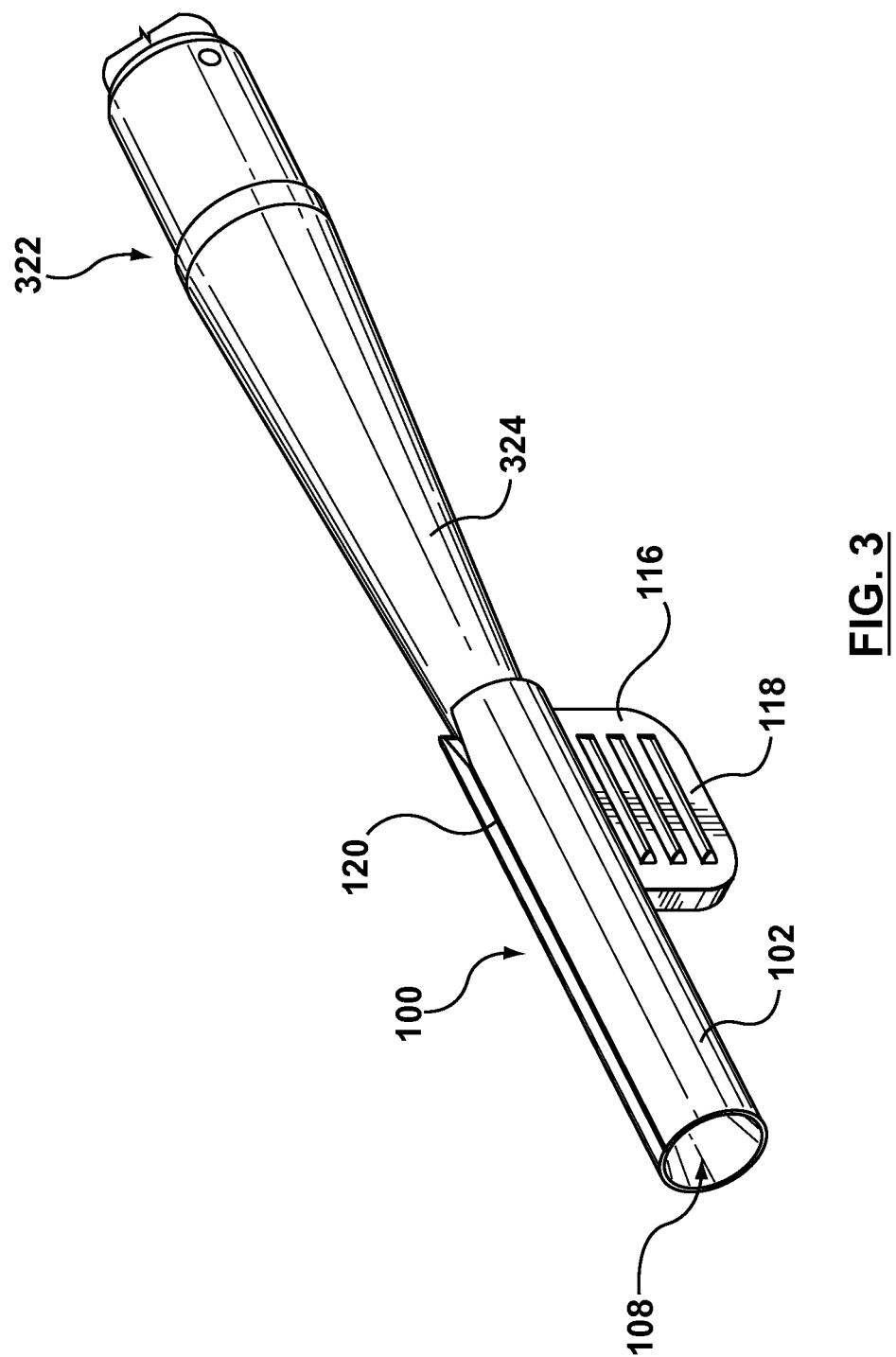
FIG. 3 is a perspective view of the guidewire funnel tool of FIG. 1 placed over a tapered distal tip of a catheter.
Figure 4:
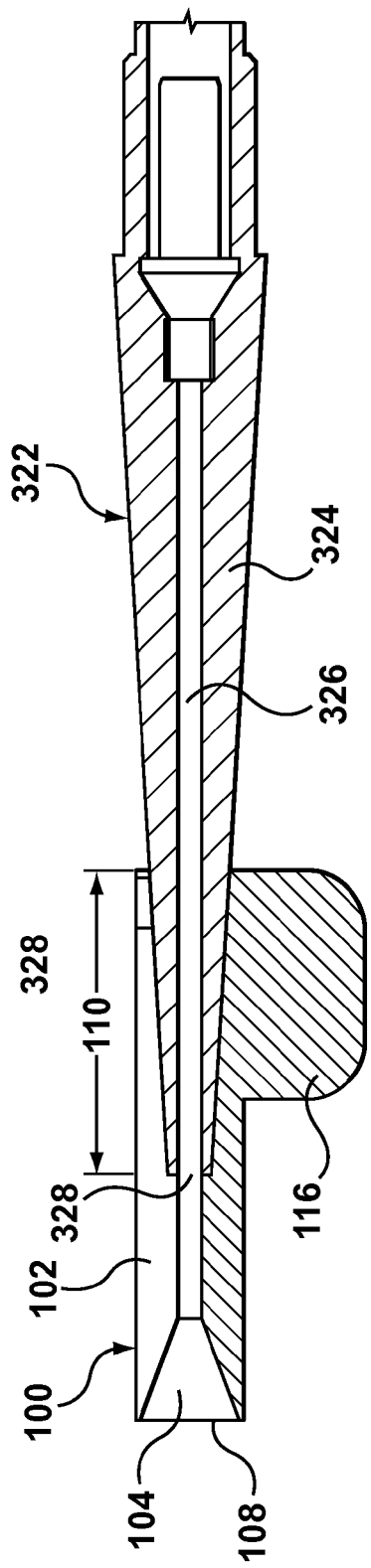
FIG. 4 is a sectional side view of the guidewire funnel tool as shown in FIG. 3.

Guidewire insertion end 108 of guidewire funnel tool 100 is adapted to receive a guidewire and catheter insertion end 106 of guidewire funnel tool 100 is adapted to receive the tapered distal tip of a catheter such that guidewire funnel tool 100 may be utilized to guide or thread a guidewire into a guidewire lumen of the catheter. More particularly, referring to FIGS. 3-4, a distal tip 324 of a catheter 322 is shown inserted within proximal section 110 of guidewire funnel tool 100. Catheter 322 may be any type of catheter or delivery system that has a guidewire lumen 326 and a distal guidewire port 328 adapted to receive a guidewire. In FIG. 1, distal tip 324 is shown as a generally conical component that tapers in a distal direction and is shaped as such to aid in tracking the catheter through the vasculature with minimal trauma to surrounding tissue. The distally-extending taper of proximal section 110 fits over and substantially matches the profile of conical catheter tip 324 with a distalmost surface of distal tip 324 abutting or seating against shoulder 113 of proximal section 110. By substantially matching the tapered profile of catheter tip 324, guidewire funnel tool 100 couples to the distal catheter tip via a tight interference or friction fit. Due to the matching tapers of guidewire funnel tool 100 and catheter tip 324, the guidewire funnel tool 100 is essentially locked onto catheter 322 and remains securely attached to the catheter during use while still retaining the ability to be pulled off catheter 322 after use. When positioned as shown in FIGS. 3 and 4, there is a smooth transition between lumen 104 of guidewire funnel tool 100 and guidewire lumen 326 of catheter 322. Once catheter 322 is properly inserted within guidewire funnel tool 100, guidewire lumen 326 of catheter 322 is substantially aligned with middle section 112 of lumen 104 of guidewire funnel tool 100.

Figure 5:
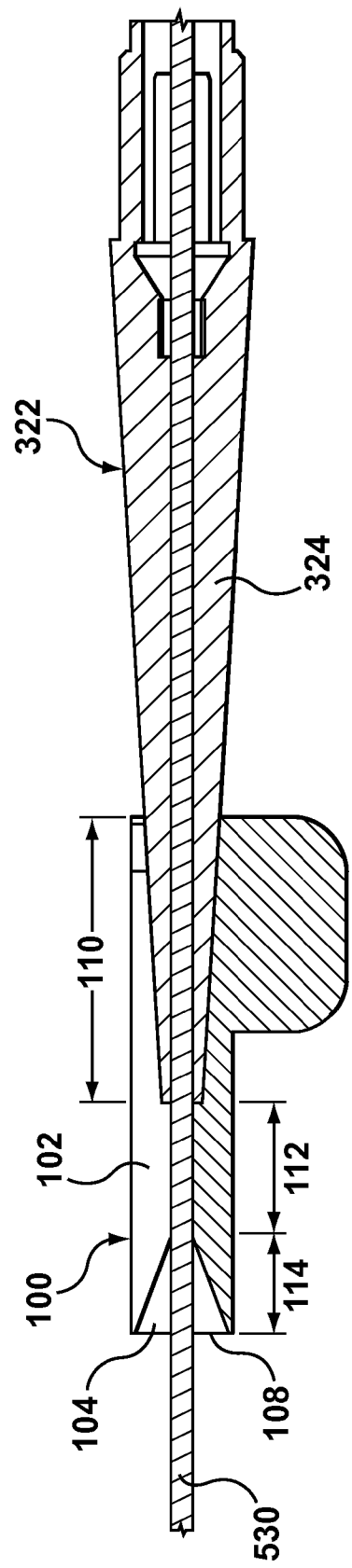
FIG. 5 is a sectional side view of the guidewire funnel tool as shown in FIG. 4 with a guidewire extending through the guidewire funnel tool and into a guidewire lumen of the catheter.

Referring now to FIG. 5, a guidewire 530 is shown extending through guidewire funnel tool 100 into guidewire lumen 326 of catheter 322. In operation, a proximal end of guidewire 530 is inserted into guidewire insertion end 108 of guidewire funnel tool 100 and received within tapered distal section 114 that serves to direct or funnel guidewire 530 into straight middle section 112. Since diameter $D_1$ is preferably between 50% and 200% greater than an outer diameter of guidewire 530, a user may insert guidewire 530 into guidewire funnel tool 100 with ease. Middle section 112 straightens and stabilizes guidewire 530 prior to entry into distal guidewire port 328 of catheter 322. Guidewire 530 then passes into guidewire lumen 326 of catheter 322. Accordingly, guidewire funnel tool 100 may be utilized to ease cannulation of guidewire lumen 326.

During a therapeutic or diagnostic percutaneous procedure, a guiding catheter or sheath (not shown) is typically first inserted through an incision and into a femoral artery, for example, of a patient. A clinician typically then introduces and advances a guidewire through the guiding catheter and the vasculature to a treatment site such that a catheter may then be subsequently tracked thereover to the treatment site. A catheter is typically backloaded onto the guidewire via a distal guidewire port. Guidewire funnel tool 100, as previously described, is used to ease the backloading of the catheter onto a proximal end of the indwelling guidewire. More particularly, proximal section 110 of guidewire funnel tool 100 is placed over the distal tip of the catheter with distal section 114 being positioned to receive the proximal end of the indwelling guidewire. The guidewire is directed through the guidewire funnel tool and into the distal guidewire port of the catheter via middle section 112 of lumen 104. After the proximal end of the guidewire is accessible by the clinician from a proximal guidewire port of the catheter, whether via a full length guidewire lumen or a rapid exchange guidewire lumen of the catheter, the guidewire funnel tool is removed such that the catheter may be tracked over the indwelling guidewire to the treatment site.

In an embodiment, guidewire funnel tool 100 may be provided on, stored, and shipped with a catheter in order to prepare the catheter in readiness for set-up and use by a physician. In another embodiment, guidewire funnel tool 100 may be shipped separately from a catheter and a physician may place guidewire funnel tool 100 onto a catheter prior to use. Due to being removable, guidewire funnel tool 100 may be re-sterilized and re-used in several successive procedures.

Figure 6:
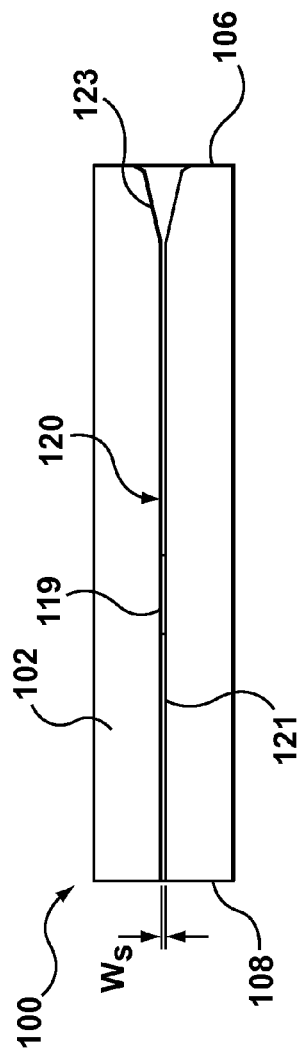
FIG. 6 is a top view of the guidewire funnel tool of FIG. 1 illustrating a longitudinal slot extending along the length of the guidewire funnel tool.

Guidewire funnel tool 100 is removable from a loaded catheter, which is a catheter having a guidewire running therethrough, due to an area of weakness 120 that extends within the wall of loading coupler 102 along the entire length thereof on a side opposite grip tab 116. As noted above, grip tab 116 is positioned along loading coupler 102 proximate catheter insertion end 106 in order to provide better leverage when removing tool 100. More particularly, referring to FIG. 6, area of weakness 120 may be a slit or slot having a width $W_S$ and a depth that extends through a wall of loading coupler 102, i.e., from the outside surface to the inside surface thereof. Slot 120 includes a straight cut, opening, or aperture in the form of one or more longitudinal lines provided by cutting through the wall of loading coupler 102. In one embodiment, width $W_S$ is approximately 0.005 inches. Area of weakness 120 allows opposing edges 119 and 121 to be pulled apart so that loading coupler 102 can be peeled off or removed from a catheter after guidewire funnel tool 100 has been utilized to successfully direct a guidewire into the guidewire lumen thereof. Due to the pliable and flexible material of loading coupler 102, guidewire funnel tool 100 transversely pulls or peels off the catheter and guidewire combination when grip tab 116 is pulled away from the catheter. Further, the pliable and flexible material of loading coupler 102 renders guidewire funnel tool 100 reusable because opposing edges 119 and 121 of slot 120 may be repeatedly pulled apart to place loading coupler 102 around several successive catheter tips. In one embodiment, slot 120 may include a flared or V-shaped end 123 having a greater width that width $W_S$ which allows loading coupler 102 to more easily stretch around a catheter tip during use and be removed from the catheter tip after cannulation of the catheter guidewire lumen.

Figure 7:
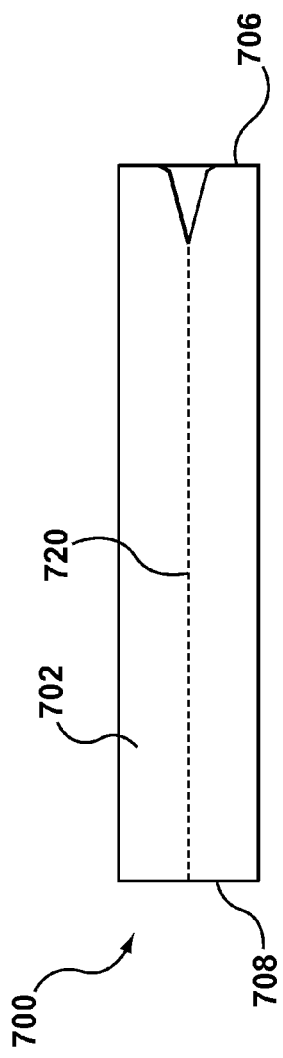
FIG. 7 is a top view of a guidewire funnel tool of FIG. 1 according to another embodiment hereof, wherein the guidewire funnel tool includes a plurality of perforations extending along the length of the guidewire funnel tool.
Figure 8:
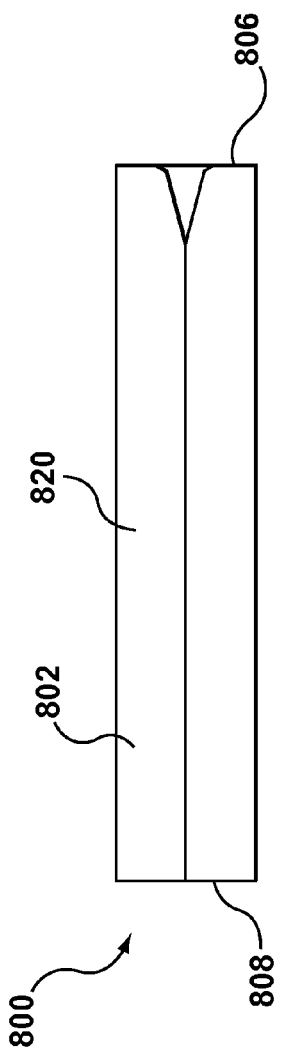
FIG. 8 is a top view of a guidewire funnel tool of FIG. 1 according to yet another embodiment hereof, wherein the guidewire funnel tool includes a groove extending along the length of the guidewire funnel tool.

In other embodiments hereof, a guidewire funnel tool may be a single-use device that is provided with a single-use catheter. More particularly, FIGS. 7 and 8 illustrate embodiments in which the guidewire funnel tool is not reusable. FIG. 7 illustrates a guidewire funnel tool 700 having a loading coupler 702 with an area of weakness 720 extending from guidewire insertion end 708 to catheter insertion end 706 thereof. Area of weakness 720 is a plurality of perforations that may be ripped apart by the user to remove guidewire funnel tool 100 from a catheter after guidewire funnel tool 700 has been utilized to successfully direct a guidewire into the guidewire lumen of the catheter. In the embodiment of FIG. 8, a guidewire funnel tool 800 having a loading coupler 802 with an area of weakness 820 extending from guidewire insertion end 808 to catheter insertion end 806 thereof is shown in which the area of weakness 820 is a groove that may be ripped apart by the user to remove guidewire funnel tool 800 from a catheter after guidewire funnel tool 100 has been utilized to successfully direct a guidewire into the guidewire lumen of the catheter. In contrast to slot 120 which extends completely through the wall of loading coupler 102, groove 820 has a depth that extends only partially within the wall of loading coupler 102 and thus does not extend completely through the outside surface to the inside surface of loading coupler 802.

FIGS. 9 and 10 illustrate another embodiment hereof that includes a feature that further secures the guidewire funnel tool in place over the distal tip of the catheter during use. Similar to guidewire funnel tool 100, guidewire funnel tool 900 includes a grip tab 916 and a loading coupler 902 having a continuous lumen 904 that extends the entire length thereof. Lumen 904 includes a guidewire insertion port 908, a tapering distal section 914, a straight middle section 912, a tapering proximal section 910 and a catheter insertion port 906 for receiving and directing a guidewire into a guidewire lumen of a catheter. In this embodiment, tapered proximal section 910 includes a circumferential protrusion or rib 940 formed on an inner surface of loading coupler 902. As shown in FIG. 10, a catheter 1022 includes a corresponding or mating circumferential groove or channel 1042 formed on an outer surface of conical distal tip 1024. When distal tip 1024 is slid within catheter insertion port 906 of guidewire funnel tool 900 to be seated within tapered proximal section 910 such that guidewire port 1028 of catheter 1022 abuts against and is aligned with middle section 910 of guidewire funnel tool 900, protrusion 940 fits within or snaps into groove 1042 in order to couple the guidewire funnel tool with the distal catheter tip. The mating groove and protrusion aids in securing guidewire funnel tool 900 in place over catheter 1022 during use but does not affect the removability of guidewire funnel tool 900.

In an embodiment, protrusion 940 is integrally formed on the inner surface of loading coupler 902 as a single molded component. In another embodiment, protrusion 940 and loading coupler 902 may be two or more separate components of the same or different materials that are coupled together via any suitable mechanical method such as via an adhesive. For example, protrusion 940 may be a band that is attached to the inner surface of the loading coupler.

While various embodiments have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An apparatus to aid in inserting a guidewire into a guidewire lumen of a catheter, the apparatus comprising:
   a pliable loading coupler having a catheter insertion end, a guidewire insertion end, and a continuous lumen extending therebetween, the continuous lumen including a guidewire receiving portion, and catheter receiving portion, and a middle portion disposed between the guidewire receiving portion and the catheter receiving portion,
      wherein in the guidewire receiving portion the lumen tapers from the guidewire insertion end towards the middle portion to receive and direct an end of the guidewire into the apparatus,
      wherein in the catheter receiving portion the lumen tapers from the catheter insertion end towards the middle portion to receive and couple with a correspondingly tapered distal tip of the catheter, wherein a protrusion extends from an interior surface of the catheter receiving portion of the lumen and is configured to mate with a corresponding groove in an exterior surface of the catheter, and
      wherein in the middle portion the lumen has a constant diameter to straighten and stabilize the guidewire received from the guidewire receiving portion of the lumen prior to entry of the guidewire into the guidewire lumen of the catheter being held in the catheter receiving portion of the lumen;
   a longitudinally-extending area of weakness formed along a length of the pliable loading coupler; and
   a tab radially extending from the pliable loading coupler, wherein the tab is adapted to be gripped by a user in order to remove the pliable loading coupler from the catheter via the area of weakness.

2. The apparatus of claim 1, wherein the tab includes a plurality of tactile gripping elements formed on a surface thereof.

3. The apparatus of claim 1, wherein the area of weakness is a slot that extends through a wall of the loading coupler.

4. The apparatus of claim 1, wherein the area of weakness is a line of perforations.

5. The apparatus of claim 1, wherein the area of weakness is a groove that partially extends through a wall of the loading coupler.

6. The apparatus of claim 1, wherein the pliable loading coupler and tab are integrally formed from one piece of material.

7. The apparatus of claim 6, wherein the material is elastomeric.

8. The apparatus of claim 1, wherein a tight interference fit couples the proximal section of the loading coupler to the correspondingly tapered distal tip of the catheter.

9. A system to aid in backloading a catheter onto a guidewire, the system comprising:
   a catheter having a guidewire lumen extending therethrough; and
   a guidewire funnel tool removably placed over a tapered distal tip of the catheter, wherein the guidewire funnel tool includes
      a pliable loading coupler having a continuous lumen extending therethrough from a guidewire insertion end to a catheter insertion end of the loading coupler, the continuous lumen including a guidewire receiving portion, a middle portion, and a catheter receiving portion, wherein the lumen in the guidewire receiving portion tapers from the guidewire insertion end towards the middle portion, the lumen in the catheter receiving portion tapers from the catheter insertion end towards the middle portion, and the lumen in the middle portion has a substantially constant diameter and is configured to straighten the guidewire received from the guidewire receiving portion and to direct the guidewire into the guidewire lumen of the catheter within the catheter receiving portion,
      an area of weakness formed along a length of the loading coupler, and
      a tab radially extending from the pliable loading coupler, wherein the tab is adapted to be gripped by a user in order to remove the pliable loading coupler from the catheter via the area of weakness, and
      wherein a protrusion is formed within an interior surface of the catheter receiving portion of the lumen of the guidewire funnel tool and a mating groove is formed on an exterior surface of the tapered distal tip of the catheter and wherein the protrusion is sized to snugly fit within the groove in order to couple the catheter receiving portion to the correspondingly tapered distal tip of the catheter.

10. The system of claim 9, wherein a tight interference fit couples the proximal section of the loading coupler to the correspondingly tapered distal tip of the catheter.

11. The system of claim 9, wherein the groove and protrusion are circumferential.

12. The system of claim 9, wherein the tab includes a plurality of tactile gripping elements formed on a surface thereof.

13. The system of claim 9, wherein the area of weakness is a slot that extends through a wall of the loading coupler.

14. The system of claim 9, wherein the area of weakness is a line of perforations.

15. The system of claim 9, wherein the area of weakness is a groove that partially extends within a wall of the loading coupler.

16. The system of claim 9, wherein the pliable loading coupler and tab are integrally formed from one piece of material.

17. The system of claim 16, wherein the material is elastomeric.

* * * * *